(12) United States Patent
DiMarzio et al.

(10) Patent No.: US 7,792,570 B2
(45) Date of Patent: Sep. 7, 2010

(54) OPTO-ACOUSTIC SIGNAL DETECTION WITH COHERENT CONFOCAL MICROSCOPY

(75) Inventors: Charles A. DiMarzio, Cambridge, MA (US); Luis A. Nieva, Lima (PE)

(73) Assignee: Northeastern University, Boston, MA (US)

( * ) Notice: Subject to any disclaimer, the term of this patent is extended or adjusted under 35 U.S.C. 154(b) by 1391 days.

(21) Appl. No.: 11/101,111

(22) Filed: Apr. 7, 2005

(65) Prior Publication Data

US 2005/0228292 A1 Oct. 13, 2005

Related U.S. Application Data

(60) Provisional application No. 60/560,071, filed on Apr. 7, 2004.

(51) Int. Cl.
*A61B 6/00* (2006.01)
(52) U.S. Cl. ........................ 600/476; 356/484
(58) Field of Classification Search ................ 600/476; 356/351, 484; 606/6
See application file for complete search history.

(56) References Cited

U.S. PATENT DOCUMENTS 5,323,779 A * 6/1994 Hardy et al. ................ 600/411
5,883,717 A * 3/1999 DiMarzio et al. ........... 356/491
5,995,867 A * 11/1999 Zavislan et al. ............. 600/476
6,020,963 A 2/2000 DiMarzio .................... 356/491
6,151,127 A * 11/2000 Kempe ........................ 356/484

OTHER PUBLICATIONS

D.O. Hogenboom and C.A. DiMarzio, "Quandrature Detection of a Doppler Signal", Applied Optics, 37(13), pp. 2569-2572; 1998.

* cited by examiner

*Primary Examiner*—Long V Le
*Assistant Examiner*—Saurel J Selkin
(74) *Attorney, Agent, or Firm*—Weingarten, Schurgin, Gagnebin & Lebovici LLP

(57) ABSTRACT

A microscopy apparatus includes a heating source to provide a pulse of heating energy focused on a target to heat a localized region of the target, such as human tissue, to generate motion. A measuring source provides a measuring light beam focused on the target. A coherent confocal microscopy assembly focuses the measuring light beam on the target and returns a reflected signal from the target. A detection assembly receives the reflected signal from the target and detects a Doppler shift of the reflected signal. A scanning assembly scans pulses from the heating source over the target and scans the measuring light beam from the measuring source over the target to build up an image of a plane of the target.

19 Claims, 6 Drawing Sheets

OPTO-ACOUSTIC SIGNAL DETECTION WITH COHERENT CONFOCAL MICROSCOPY

CROSS REFERENCE TO RELATED APPLICATIONS

This application claims the benefit under 35 U.S.C. §119 (e) of U.S. Provisional Application No. 60/560,071, filed Apr. 7, 2004, the disclosure of which is incorporated by reference herein.

STATEMENT REGARDING FEDERALLY SPONSORED RESEARCH OR DEVELOPMENT

Development of the present invention was supported, in part, by CenSSIS, the Center for Subsurface Sensing and Imaging Systems, under the Engineering Research Center Program of the National Science Foundation (Award number EEC-9986821).

BACKGROUND OF THE INVENTION

Optical confocal microscopy has become a popular technique to produce images in biological tissue with lateral resolutions of 0.5 to 1 µm and comparable axial resolutions. The technique collects reflectance or fluorescence images ex vivo and is rapidly growing as an in vivo diagnostic tool. Applications include imaging basal cell carcinomas, assisted Moh's surgery, and studies of the oral mucosa. A disadvantage of this technique is the lack of penetration at depths higher than 300 to 350 µm in human skin, because of multiple scattering contributing to the optical noise as well as discontinuities in the optical properties at the dermo-epidermal junction and below.

SUMMARY OF THE INVENTION

The present invention relates to generating a heterodyne optical signal by inducing particle displacements within a medium such as human tissue. More particularly, a heating source directs focused pulses of light or ultrasound energy at a target, such as human skin, to generate particle displacement by localized heating and consequent expansion of the target. Target particle displacement detection is performed with a coherent confocal microscope using a measuring source that directs a continuous beam of light at the target. As the target expands, the Doppler shift of the returning signal of the coherent confocal microscope is detected using interferometric techniques.

DESCRIPTION OF THE DRAWINGS

The invention will be more fully understood from the following detailed description taken in conjunction with the accompanying drawings in which.

DETAILED DESCRIPTION OF THE INVENTION

Figure 1:
FIG. 1 is a schematic illustration of a laser light source focused on tissue to induce localized heating.
Figure 2:
FIG. 2 is a schematic illustration showing heating of a localized region.
Figure 3:
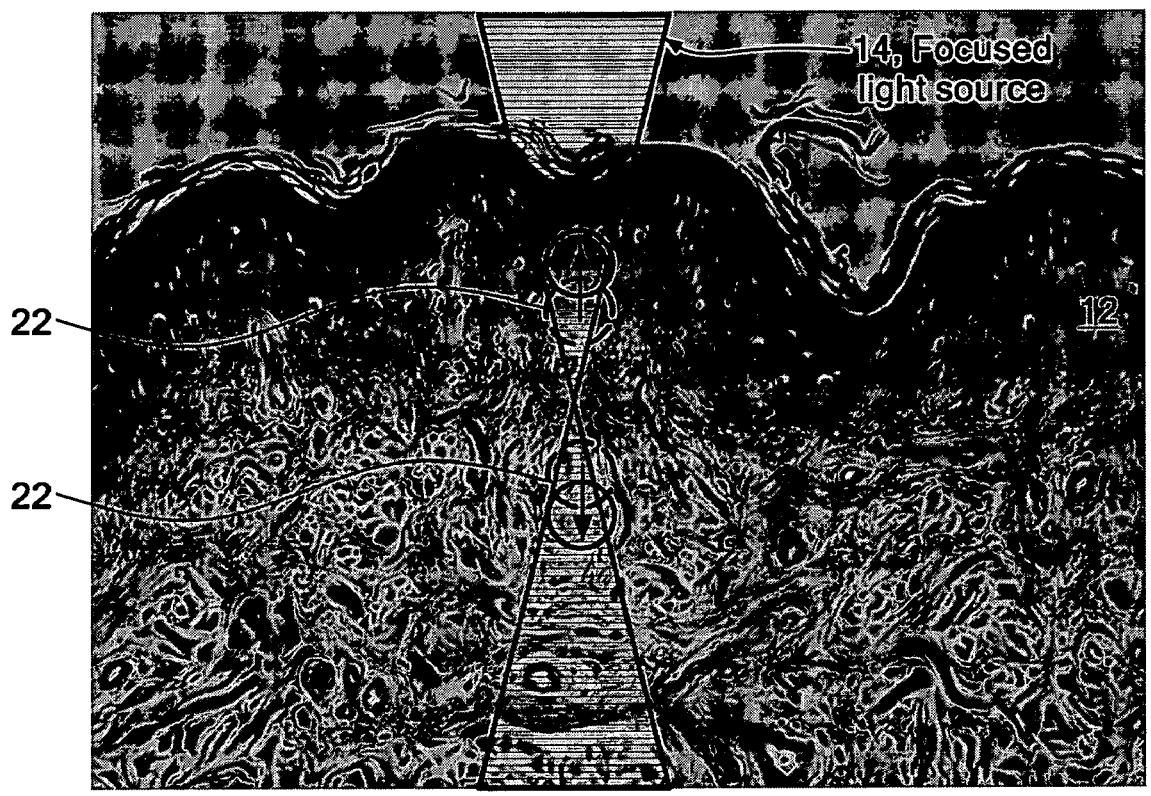
FIG. 3 is a schematic illustration showing particle motion caused by heating.

FIGS. 1-4 illustrate the present invention utilizing a patient tissue sample 12 as the target. A light beam pulse 14 from a heating source, such as a laser or an ultrasound generator, is focused within the tissue, for example, in the dermis. The focused light beam heats the tissue in a localized region, indicated schematically by the circle 18 in FIG. 2. As the tissue heats up, the tissue in the localized region expands. Particles 22, indicated schematically by the dashed circles, move outwardly. FIG. 3 schematically illustrates the outward motion of two particles moving in the direction of the arrows. When the pulse from the heating source is turned off, the tissue cools down. The tissue expansion decays exponentially as its temperature returns to ambient, the temperature of the surrounding tissue, which serves as a heat sink. The tissue must be heated sufficiently rapidly to expand locally, but not so rapidly that it generates acoustic waves that radiate to the surrounding tissue rather than remaining localized. A heating pulse on the order of 1 us has been found to be suitable. A discussion of thermal expansion concepts can be found in Nieva, Alex, Matthew Bouchard, and Charles A. DiMarzio, "Optoacoustic signal detection with a coherent confocal microscope setup," Proc. SPIE 5697 pp. 313-321. 2005, incorporated by reference herein in full.

Figure 4:
FIG. 4 is a schematic illustration showing a coherent confocal laser light beam for use with Doppler detection of motion.

FIG. 4 illustrates schematically a focused light beam 26 from a measuring source, such as a laser. The measuring source is on continuously while the heating source is pulsed. The relative signal from the measuring source returned from the target is indicative of the particle's thermal expansion. As the tissue expands, the Doppler shift of the returning signal is detected, as described further below.

Figure 5:
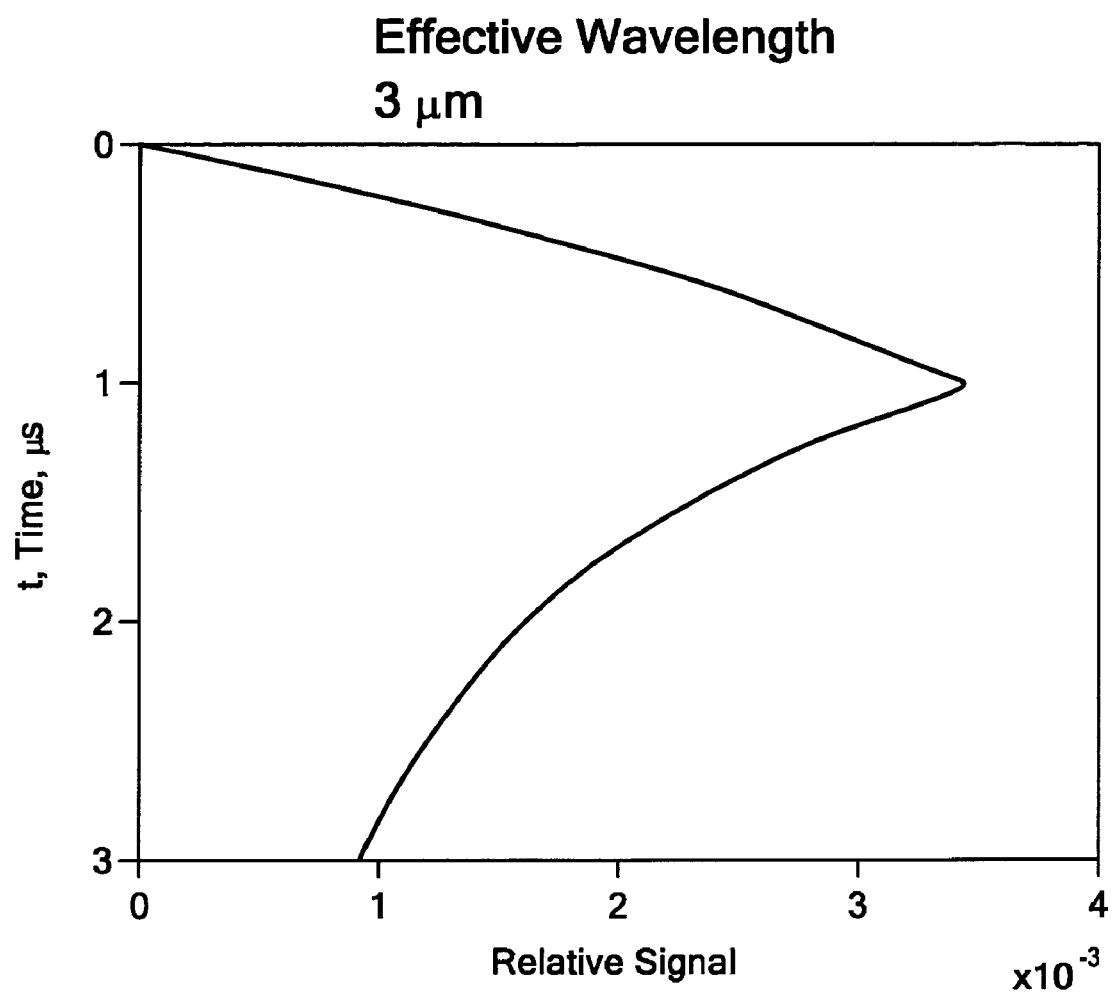
FIG. 5 is a graph illustrating the relative signal from the confocal laser light beam during and after a pulse from the heating source.

Referring to the graph of FIG. 5, detection of the return signal begins just before the pulse from the heating source is turned on. In the example shown, the pulse from the heating source is on for 1 µs, beginning at t=0. The relative signal is derived from the phase of the scattered light. It can be seen to increase during the pulse. When the pulse is turned off, the tissue begins to cool exponentially, and the relative signal decreases.

Figure 6:
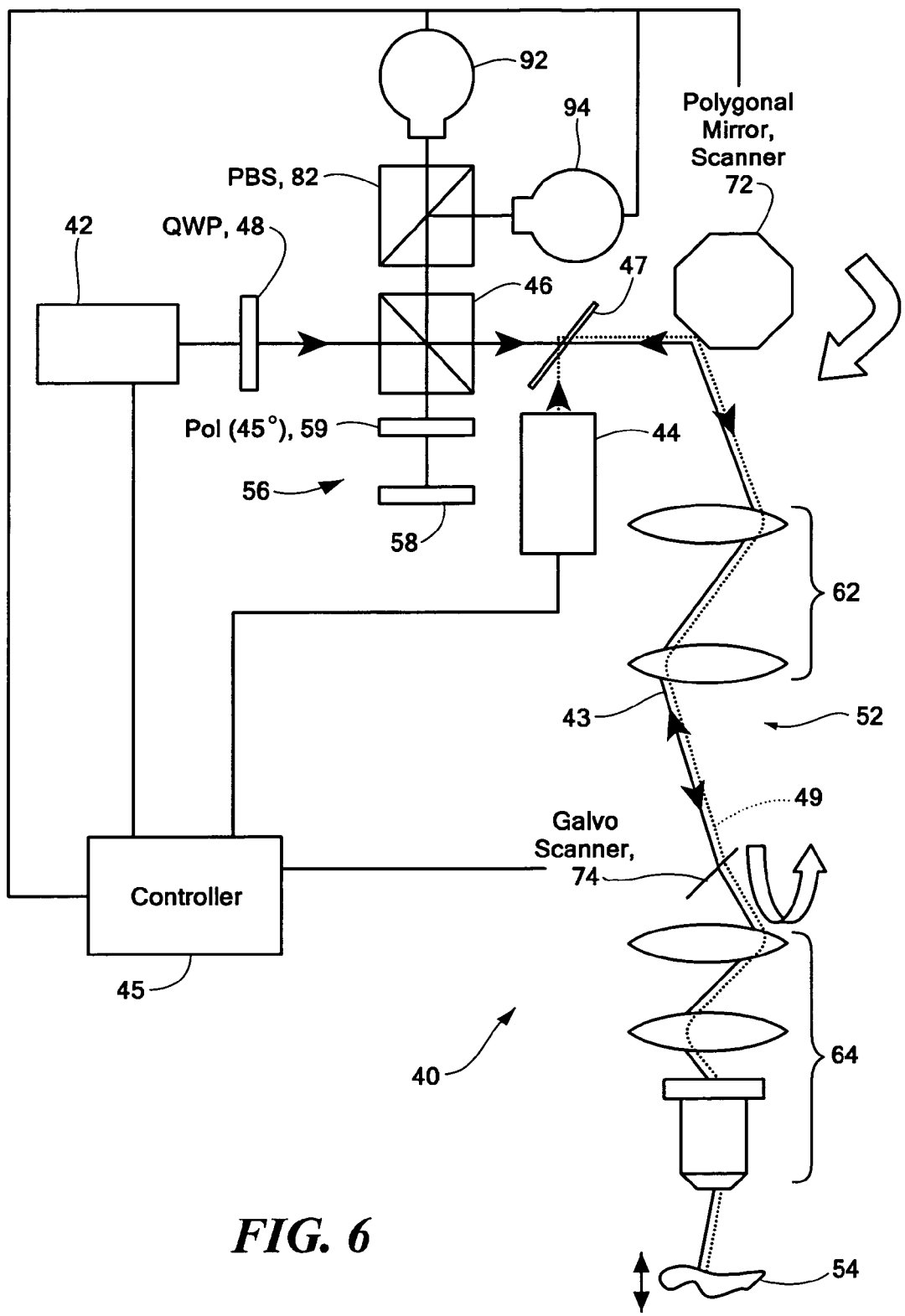
FIG. 6 is a schematic illustration of an apparatus for signal detection with confocal microscopy.

FIG. 6 illustrates an apparatus 40 according to the present invention. A measuring source 42 transmits a beam of light, indicated schematically by a solid line 43 in FIG. 6, to the target, continuously or spanning the duration of the pulse from the heating source. A heating source 44 transmits a pulse of heating energy, indicated schematically by a dashed line 49 in FIG. 6, to the target to heat a localized region. A partially transmitting and partially reflecting surface 47 directs the beam from the heating source onto the path of the measuring source. The measuring source and the heating source can employ lasers of any suitable wavelength. The wavelengths can be different. Multiple wavelengths can be used for the measurement laser. For applications imaging human tissue, hemoglobin absorbs shorter (blue) wavelengths and water absorbs longer (red) wavelengths. When imaging human tissue, wavelengths in the range of 600 to 900 nm are generally suitable. In an exemplary embodiment, the measuring laser wavelength can be in the mid portion of this range, and the heating laser wavelength can be nearer the ends of this range. A dye can be used that absorbs a particular wavelength, and in this case the heating laser would use this wavelength. Other wavelengths can be used, depending on the application. The heating source can alternatively be a high-frequency ultrasound generator. Any suitable controller 45 can be provided to control operation of the measuring source and the heating source.

From the measuring source 42, the beam of light is directed to a beamsplitter 46. The beamsplitter 46 is a 50% reflecting, non-polarizing beamsplitter. A quarter wave plate 48 may be inserted in the path between the measuring source and the beamsplitter 46. The beamsplitter splits the beam from the measuring source onto two arms, a first or measurement arm 52 to the target 54 and a second or reference arm 56 to a reflecting surface 58. The second arm provides a reference beam or signal unaffected by the target.

The measurement arm 52 includes components of a coherent confocal microscope. For example, in the embodiment illustrated, the measuring beam passes through first and second lens assemblies 62, 64 to the target 54. The beam reflects from the moving target and a Doppler-shifted return signal travels back along the measurement arm 52 through the lens assemblies to the beamsplitter 46. The lens assemblies of a coherent confocal microscope are known to those of skill in the art and need not be described in detail. A raster scan is generated by, for example, two orthogonal, or X and Y, scanners 72, 74 in communication with the controller 45. One scanner provides a fast scan of the beam to generate a row or line of pixels. The other scanner provides a slower scan to generate the multiple lines of the raster scan. The heating source is pulsed at a rate greater than the faster scan rate so that a Doppler shifted signal can be generated for each pixel in the raster. Any desired raster size, such as 512×512 pixels, may be generated.

In the embodiment illustrated, a polygonal mirror scanner is provided for the faster scan, and a galvo scanner is provided for the slower scan. It will be appreciated that the scanner configuration can vary. For example, the scanner configuration can utilize two galvo scanners. Alternatively, the sample can be moved to generate the raster scan.

The reference signal and the return signal are recombined at the beamsplitter 46. The reference beam light, reflected from the reflecting surface 58, is linearly polarized at 45° by polarizer 59 with respect to the plane of incidence of the beamsplitter. The signal light, passing through the lens assemblies on the measurement arm 52, scattering from the moving target, and returning, is assumed to retain its polarization. If not, polarizing components may be used to select the part of the light that does retain polarization.

The recombined beams are then separated into two components by a polarizing beamsplitter 82 and directed to the detectors 92, 94, in communication with the controller 45. Thus, the linear reference beam is in the same phase on both channels, while the circular signal beam is a cosine on one channel and a sine on the other, as indicated by the following equations:

$$I=|E_{sig}+E_{ref}|^2$$

and $$Q=|iE_{sig}+E_{ref}|^2$$

where I and Q represent the in-phase and quadrature components.

Each signal in the above two equations varies with time as the phase of the signal field changes. Subtracting the values of these signals before the heating pulse, we obtain only the contributions caused by the particle motion. Then the phase of the signal is the arctangent of the ratio of this time-varying part of I and the time-varying part of Q. The particle displacement is given by the change in phase divided by the wavelength and multiplied by $2\pi$. Multiple laser wavelengths can be used to resolve the ambiguities in particle position. Optical quadrature interferometry to obtain in-phase and quadrature information is further described in U.S. Pat. Nos. 5,883,717 and 6,020,963.

Alternatives to the above embodiment include placing the polarizer 46 in the measurement arm instead of the reference arm, and using a modified Mach Zehnder interferometer, as is known in laser Doppler systems.

Although quadrature detection has been illustrated in the embodiment described above, other techniques for generating phase information can be used, as will be appreciated by one of skill in the art. For example, the reference beam can be generated from a separate offset laser or a Bragg shifted transmitter. In another option, a tilted reference with multiple detectors can be provided.

The present invention is useful for medical imaging of human skin and for mechanical and optical tissue characterization. Applications include skin cancer detection and imaging, characterization of contact dermatitis, and study of embryo viability. The present invention provides images at longer depths than confocal microscopy alone, which lacks depth of penetration. The use of ultrasound to induce particle displacements inside biological tissue is non-invasive and safe for clinical use.

The invention is not to be limited by what has been particularly shown and described, except as indicated by the appended claims.

What is claimed is:

1. A microscopy apparatus comprising:
   a heating source configured to provide a pulse of heating energy focused on a target area to generate energy sufficient to heat the target area sufficiently to generate motion of particles in the target area without generating acoustic waves to a region surrounding the target area;
   a measuring source configured to provide a measuring light beam focused on the target;
   a coherent confocal microscopy assembly configured to focus the measuring light beam on the target while the particles are in motion and configured to return a Doppler-shifted reflected signal from the target;
   a detection assembly configured to receive the reflected signal from the target and configured to detect the Doppler shift of the reflected signal; and
   a controller in communication with the heating source and the measuring source and the detection system, that is configured to provide the measuring light beam spanning the duration of the pulse from the heating source, and to determine the Doppler shift in conjunction with the detection assembly to provide image data of the target.

2. The apparatus of claim 1, wherein the coherent confocal microscopy assembly further comprises a scanning assembly configured to scan pulses from the heating source over the target and to scan the measuring light beam from the measuring source over the target.

3. The apparatus of claim 1, wherein the measuring source comprises a laser.

4. The apparatus of claim 1, wherein the heating source comprises a laser.

5. The apparatus of claim 1, wherein the heating source comprises an ultrasound generator.

6. The apparatus of claim 1, comprising an optical component configured to direct the pulse from the heating source onto a path from the measuring source to the target.

7. The apparatus of claim 1, further comprising a first beamsplitter disposed to receive the measuring light beam from the measuring source and split the measuring beam into a measurement arm directed to the target and a reference arm directed to a reflecting surface and to recombine Doppler-shifted reflected light from the target and reflected light from the reflecting surface.

8. The apparatus of claim 7, further comprising a second beamsplitter disposed to separate recombined light from the first beamsplitter into two components and direct the components to the detection assembly.

9. The apparatus of claim 8, wherein the two components comprise an in-phase component and a quadrature component.

10. A method for imaging a target comprising:
    heating a localized region of the target with a pulse of energy focused on a target area to generate energy sufficient to heat the target area sufficiently to generate motion of particles by thermal expansion in the target area without generating acoustic waves to a region surrounding the target area;
    focusing a measuring light beam at the localized region of the target during the heating pulse; and
    determining a Doppler shift of a reflected measuring light beam from the target to provide image data of the target.

11. The method of claim 10, wherein the measuring light beam is on for a time spanning the duration of the motion generating pulse.

12. The method of claim 10, further comprising turning on the motion generating pulse for a time on the order of 1 μs.

13. The method of claim 10, wherein the motion generating pulse comprises a pulse of laser light.

14. The method of claim 10, wherein the motion generating pulse comprises a pulse of ultrasound energy.

15. The method of claim 10, wherein the measuring light beam comprises a laser beam.

16. The method of claim 10, further comprising directing the motion generating pulse along a same path as the measuring light beam.

17. The method of claim 10, further comprising combining a reference light beam with the reflected measuring light beam and separating the combined light beam into an in-phase component and a quadrature component.

18. The method of claim 10, further comprising scanning the motion generating pulse and the measuring light beam across the target to generate a two-dimensional image.

19. The method of claim 10, wherein the target comprises human tissue.

* * * * *